(12) United States Patent
Woods et al.

(10) Patent No.: US 10,407,223 B1
(45) Date of Patent: Sep. 10, 2019

(54) DEVICE AND DRAPING METHOD FOR FACILITATING INTRODUCTION OF A NON-STERILE CONTAINER INTO A STERILE ENVIRONMENT

(71) Applicant: REPLIGEN CORPORATION, Waltham, MA (US)

(72) Inventors: William Woods, Rockwall, TX (US); Michelle Fleming, Dallas, TX (US)

(73) Assignee: REPLIGEN CORPORATION, Waltham, MA (US)

( * ) Notice: Subject to any disclaimer, the term of this patent is extended or adjusted under 35 U.S.C. 154(b) by 0 days.

(21) Appl. No.: 15/939,648

(22) Filed: Mar. 29, 2018

(51) Int. Cl.
| | |
|---|---|
| *B65D 47/06* | (2006.01) |
| *B65D 51/22* | (2006.01) |
| *B65D 83/00* | (2006.01) |
| *A61B 46/10* | (2016.01) |
| *A61B 50/30* | (2016.01) |
| *A61J 1/14* | (2006.01) |
| *A61B 50/00* | (2016.01) |

(52) U.S. Cl.
CPC .............. *B65D 47/06* (2013.01); *A61B 46/10* (2016.02); *A61B 50/30* (2016.02); *A61J 1/1443* (2013.01); *A61J 1/1475* (2013.01); *B65D 51/222* (2013.01); *B65D 83/00* (2013.01); *A61B 2050/002* (2016.02); *A61B 2050/314* (2016.02); *B65D 2251/0025* (2013.01); *B65D 2251/0093* (2013.01)

(58) Field of Classification Search
CPC . B65D 47/06; A61B 6/10; A61B 50/30; A61J 1/1443; A61J 1/1475; A61M 5/002; A61M 5/50; A61M 5/5086; A61M 25/002

USPC ............... 222/81, 82, 89, 92, 93, 86, 107; 604/408, 411, 415
See application file for complete search history.

(56) References Cited

U.S. PATENT DOCUMENTS

| | | | | |
|---|---|---|---|---|
| 3,105,613 A | * | 10/1963 | Barton | A61J 1/10 141/330 |
| 3,797,734 A | * | 3/1974 | Fleury | A61J 19/00 383/36 |
| 4,458,733 A | * | 7/1984 | Lyons | A61J 1/2089 141/1 |
| 4,898,588 A | * | 2/1990 | Roberts | A61M 3/0287 604/187 |
| 5,295,964 A | * | 3/1994 | Gauthier | A61J 1/1462 604/113 |
| 5,735,833 A | * | 4/1998 | Olson | A61H 9/0021 604/23 |
| 5,795,324 A | | 8/1998 | Morse | |
| 7,311,695 B1 | | 12/2007 | Schultz | |

(Continued)

FOREIGN PATENT DOCUMENTS

| | | |
|---|---|---|
| EP | 1293441 A1 | 3/2003 |
| WO | 2015024360 A1 | 3/2015 |
| WO | 2016127222 A1 | 8/2016 |

*Primary Examiner* — Vishal Pancholi

(57) ABSTRACT

An improved device for enabling a non-sterile container of liquid, such as, for example, a bottle to be introduced into a sterile environment. In one embodiment, the device seals the non-sterile container within a drape so that the non-sterile container can be introduced into the sterile environment. The device may include a drape having an interior cavity for receiving the non-sterile container and a cap coupled to the enclosure for coupling to the non-sterile container so that the liquid product may flow through the sterile cap.

20 Claims, 6 Drawing Sheets

(56) References Cited

U.S. PATENT DOCUMENTS

| | | | |
|---|---|---|---|
| 7,354,427 B2* | 4/2008 | Fangrow | A61J 1/2089 604/413 |
| 2002/0020636 A1* | 2/2002 | Bergamini | A61J 1/2093 206/219 |
| 2008/0058717 A1 | 3/2008 | Spector | |

* cited by examiner

DEVICE AND DRAPING METHOD FOR FACILITATING INTRODUCTION OF A NON-STERILE CONTAINER INTO A STERILE ENVIRONMENT

FIELD OF THE DISCLOSURE

The present disclosure relates generally to sterile systems, and more particularly to an improved device, system and method for facilitating the introduction of a non-sterile container containing a sterile liquid product to be introduced into a sterile environment without the need to sterilize the outer surfaces of the container.

BACKGROUND OF THE DISCLOSURE

Use of liquid products such as, for example, medications, wound lavage liquids, saline, and the like are often required in sterile environments, such as, for example, an operating room, a quarantine area, etc. In many cases these liquid products are disposed within a container or bottle, such as, for example, a glass or plastic container or bottle (used interchangeably herein without the intent to limit).

One problem associated with the use of such containers is that, while the internal contents of the container may be sterile, the exterior surfaces of the container often are non-sterile and, as such, the container cannot be introduced into the sterile environment. Sterilizing the exterior surfaces of such containers can be expensive and, depending on the sterilization technique used, can harm the liquid product contained therein. As a result, introduction of containers into the sterile environment is generally not permitted.

One current solution to this problem is to position the non-sterile container outside of the sterile environment, and to couple a long transfer tube to the container to deliver the liquid product to the application site within the sterile environment. As will be appreciated, the incorporation of a long transfer tube may be inconvenient and can be a safety hazard. In addition, the use of long runs of tubing can increase the amount of time it takes to deliver the liquid product to the patient, and can result in the wasting of quantities of liquid that remain within the tubing.

In view of these and other problems, it would be advantageous to provide an easy to use device, system and method for enabling introduction of a non-sterile container such as, for example a bottle, containing a liquid product into a sterile environment. It is with these considerations that the present disclosure is put forth.

SUMMARY OF THE DISCLOSURE

This Summary is provided to introduce a selection of concepts in a simplified form that are further described below in the Detailed Description. This Summary is not intended to identify key features or essential features of the claimed subject matter, nor is it intended as an aid in determining the scope of the claimed subject matter.

In one embodiment, the present disclosure is directed to a device for enclosing a non-sterile container to enable introduction of the container into a sterile environment. The device may include a drape having an interior cavity for receiving a non-sterile container therein and a cap coupled to the drape. The cap having a nozzle extending through the drape. The cap coupling to the non-sterile container so that a liquid within the non-sterile container can be expelled through a nozzle of the cap.

In one embodiment, the drape may include a first end and a second end, the interior cavity extending from the first end to the second end. The first end of the drape may include an opening for receiving the non-sterile container. The first end of the drape may also include a sealing mechanism for sealing the opening when the non-sterile container is positioned within the interior cavity. The sealing mechanism may be an adhesive strip.

In one embodiment, the nozzle may include a first end, a second end, and a thru-bore extending from the first end to the second end. The second end of the drape may be sealed to the cap so that the first end of the cap is positioned within the interior cavity of the drape and the nozzle extends through an opening in the drape so that the second end of the cap is positioned outside of the drape. The first end of the cap may also include a container coupling mechanism for engaging the non-sterile container positioned within the interior cavity of the drape. The container coupling mechanism may be in the form of a threaded cap, a rubber stopper, or a press-fit cap.

In one embodiment, the first end of the cap may also include a seal piercing mechanism so that, in use, coupling the cap to the non-sterile container causes the seal piercing mechanism to pierce a seal located on the non-sterile container to place the cap in fluid communication with the liquid located within the non-sterile container.

In one embodiment, the device may also include a splash guard for coupling to the cap. The splash guard may include an opening for receiving the nozzle of the cap. The nozzle may include a ridge, the splash guard engageable with the ridge when the splash guard is pressed toward the first end of the cap.

The present disclosure also discloses a method for introducing a non-sterile container containing a sterile liquid into a sterile environment. In one embodiment, the method includes inserting a non-sterile container into an interior cavity of a sterile cap and drape device, sealing the cap and drape device about the non-sterile container to seal the non-sterile container within the interior cavity of the cap and drape device, coupling a cap to the non-sterile container, and via the cap, dispensing the sterile liquid within the sterile environment.

In one embodiment, the method may further include coupling a splash guard to the cap by pressing the splash guard into engagement with a nozzle of the cap, the splash guard having an opening for receiving the nozzle therethrough, the nozzle having a ridge for seating the splash guard thereon.

In one embodiment, coupling the cap to the non-sterile container may include coupling a container coupling mechanism formed on a first end of the cap to the non-sterile container.

In one embodiment, the method may further include adhering an inner surface of the cap and drape device to an outer surface of the non-sterile container. Additionally, and/or alternatively, the method may include adhering an inner surface of the cap and drape device to the non-sterile container.

In one embodiment, sealing the cap and drape device about the non-sterile container may include adhering a portion of the cap and drape device to itself. Adhering a portion of the cap and drape device to itself may include removing a tape strip adhesive strip disposed on a flap portion of a first end of the drape, and pressing the adhesive strip and flap portion against an outer surface of the cap and drape device.

BRIEF DESCRIPTION OF THE DRAWINGS

By way of example, a specific embodiment of the disclosed device will now be described, with reference to the accompanying drawings, in which.

DETAILED DESCRIPTION

Embodiments of an improved device, system and method for enabling a container of liquid, such as, for example, a bottle of liquid product to be introduced into a sterile environment in accordance with the present disclosure will now be described more fully hereinafter with reference to the accompanying drawings, in which preferred embodiments of the present disclosure are presented.

The disclosure will proceed in relation to the description of a non-sterile container, by which is meant that the external surfaces of the container are non-sterile. It will be appreciated that in various embodiments the interior surfaces of the container will be sterilized, and that the container will hold a sterile liquid therein. The sterilized interior of the container may be sealed in any of a variety of conventional manners using an appropriate cap or other plastic, paper or metallic sealing element to maintain sterility of the container contents even in non-sterile environments In one embodiment of the disclosure, a cap and drape system may be used to enclose and/or seal a non-sterile container such as, for example, a bottle, thereby allowing the non-sterile container to be brought into a sterile environment. In some embodiments, the cap and drape system may include a drape, a housing, an enclosure or a pouch (those terms being used interchangeably herein without the intent to limit) for receiving and enclosing the non-sterile container therein, and a cap for securing to the non-sterile container so that the non-sterile container can be introduced into the sterile environment. In some embodiments that cap can include features that automatically puncture a seal of the non-sterile container when the cap is applied to the container, thus allowing the liquid product therein to be delivered to the patient via the cap and a nozzle secured thereto.

As will be appreciated, the disclosed cap and drape system provides an improved mechanism for enabling medical personnel to introduce non-sterile containers or products into a sterile environment for use therein. This enables faster delivery times of the liquid product to the patient and allows medical personnel greater access to non-sterile containers or products that cannot practically be sterilized.

Figure 1:
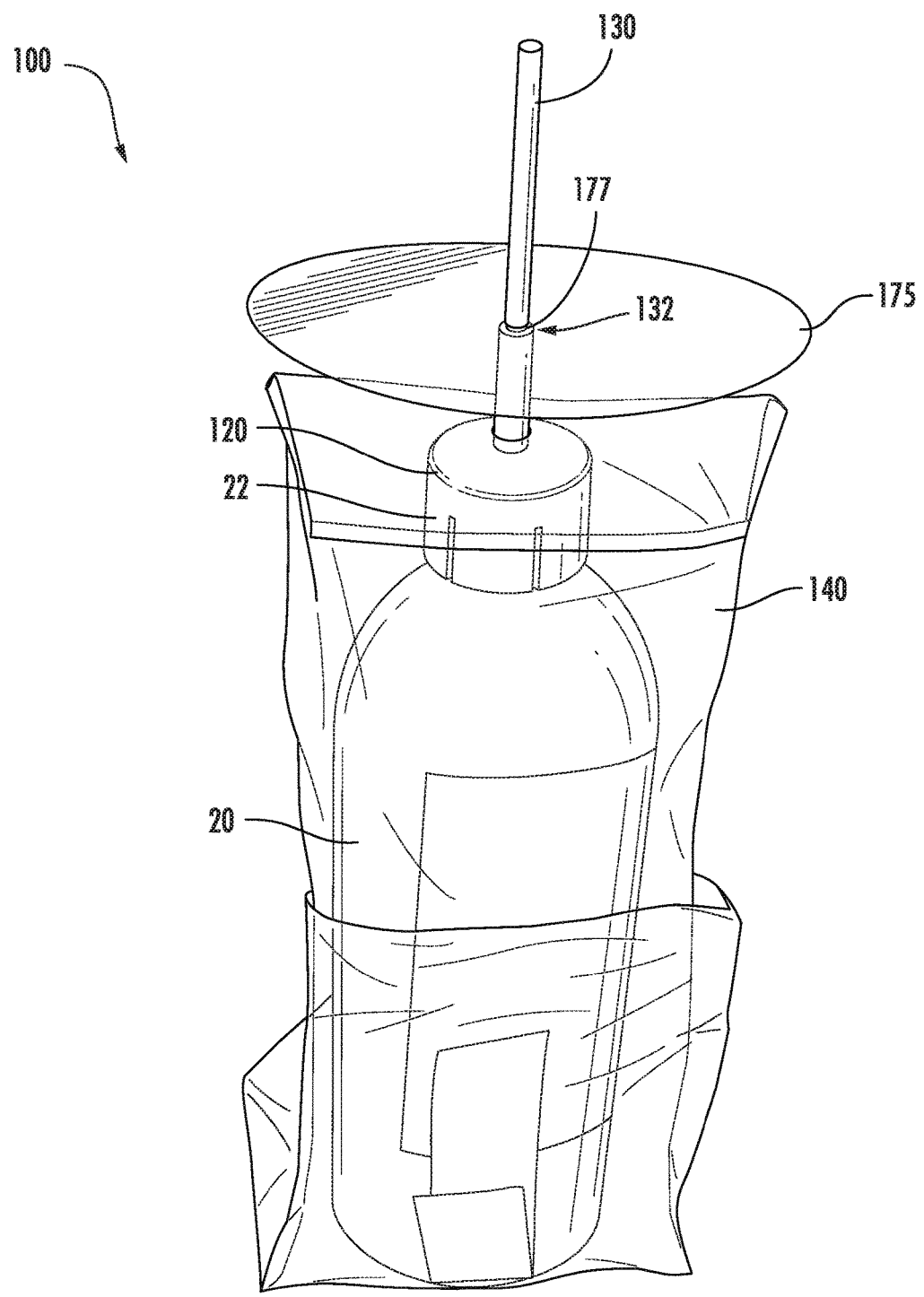
FIG. 1 illustrates a perspective view of a non-sterile container disposed within a cap and drape system according to the disclosure.
Figure 2:
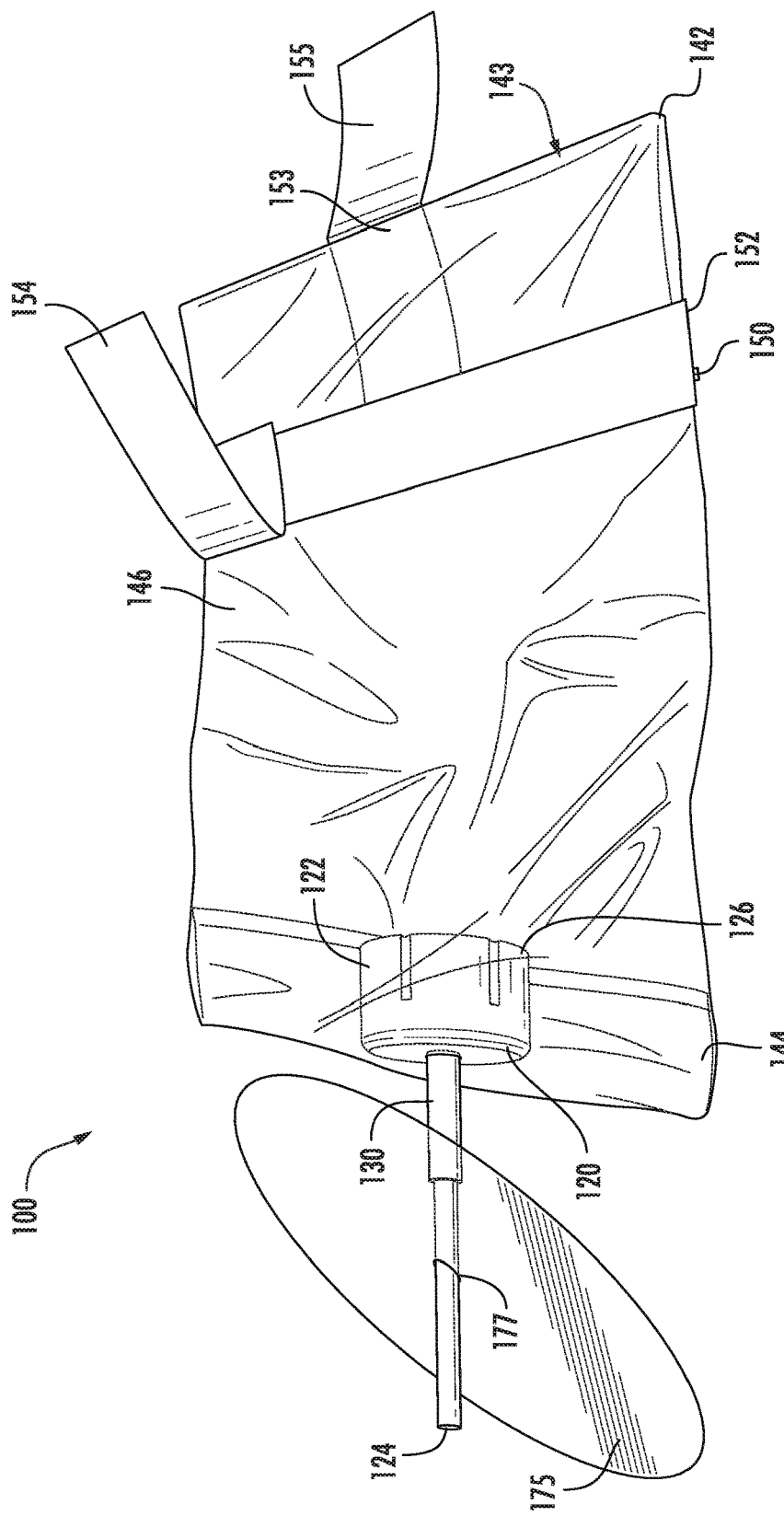
FIG. 2 illustrates a perspective view of an example embodiment of a cap and drape system according to the disclosure.

Referring now to FIGS. 1 and 2, an example embodiment of a cap and drape system 100 according to the present disclosure is illustrated. In use, the cap and drape system 100 may be pre-sterilized and delivered to the sterile environment within a sterile enclosure such as, for example, a Tyvek pouch. The cap and drape system 100 can be removed from the sterile pouch and disposed about the non-sterile container 20. Sealing the cap and drape system 100 about the non-sterile container 20 results in a sterile barrier that covers the non-sterile surfaces of the container, thus allowing the container to be introduced into a sterile environment.

As illustrated, the cap and drape system 100 may include a cap 120 and a drape or enclosure 140. As will be described in greater detail below, in use, the enclosure 140 may be sized and configured to enclose a non-sterile container 20 (e.g., a non-sterile bottle). The cap 120 may be adapted and configured to couple to the non-sterile container 20, for example, to a neck portion 22 formed on the container 20. In some non-limiting example embodiments, the cap 120 may be adapted and configured so that coupling the cap 120 to the container 20 causes the cap 120 to pierce a seal located in or on a mouth portion of the container 20 so that the liquid contained within the container 20 can be accessed. As a result of the non-sterile container 20 being entirely enclosed by the enclosure 140, the non-sterile container 20 can be introduced and used within the sterile environment without the need to separately sterilize the external surfaces of the container.

Referring to FIG. 2, the enclosure 140 is shown in a collapsed configuration (i.e., the configuration in which the enclosure will be stored within the sterile pouch prior to use). The drape or enclosure 140 may include a first end 142, a second end 144, and an interior cavity 146. The enclosure 140 may be manufactured from any suitable sterilizable material now known or hereafter developed. For example, in one embodiment, the enclosure 140 may be manufactured from a flexible plastic material. The interior cavity 146 may be sized and configured to accommodate non-sterile containers 20 (e.g., non-sterile bottles) of various sizes and/or shapes.

As illustrated, the first end 142 of the enclosure 140 may include an opening 143 for receiving the non-sterile container 20 therethrough. The first end 142 of the enclosure 140 may also include a sealing mechanism 150 for closing and/or sealing the opening 143 once the non-sterile container 20 is positioned within the interior cavity 146. The sealing mechanism 150 may be any suitable sealing mechanism, and in the non-limiting illustrated embodiment the sealing mechanism is an adhesive strip disposed on a flap portion 152 of the first end 142 of the enclosure. During use, the user can remove a tape strip 154 covering the adhesive and can fold the first end 142 of the enclosure over itself to adhere the flap portion 152 to the enclosure 140, thus sealing the enclosure around the container 20.

A second sealing mechanism 153 may also be provided on an interior surface of the enclosure 140. This second sealing mechanism 153 may enable the user to seal the enclosure 140 to an external surface of the non-sterile container 20. The second sealing mechanism 153 may be any suitable sealing mechanism, and in the non-limiting illustrated embodiment is an adhesive strip disposed on an inner surface of the enclosure 140. During use, once the non-sterile container 20 has been received within the enclosure 140, the user can remove a tape strip 155 covering the adhesive strip and can press the enclosure against the non-sterile container 20 to adhere the enclosure 140 to the container, stabilizing the enclosure around the container 20.

The second end 144 of the enclosure 140 may be attached and sealed to the cap 120. The cap 120 may be attached and sealed to the enclosure 140 by any suitable manner now known or hereafter developed including, for example, a thermal weld, a heat seal, a heat shrink sleeve, a mechanical connection or coupling, an adhesive such as, for example, double side tape or an ultraviolet (UV) adhesive, etc. Alternatively, the cap 120 can be integrally formed as part of the enclosure 140.

Referring to FIGS. 2-5, the cap 120 may include a nozzle 130. As illustrated, the cap 120 may also include a first end 122, a second end 124, and a thru-bore 125 extending from the first end 122 to the second end 124. In use, the first end 122 of the cap 120 may be located within the interior cavity 146 of the enclosure 140 while the nozzle 130 may extend through the enclosure 140 so that the second end 124 of the cap 120 is positioned outside of the enclosure 140. The first end 122 of the cap 120 may include a container coupling mechanism 126 for engaging the non-sterile container 20. In some embodiments, the container coupling mechanism 126 may couple to the neck portion 22 of the container 20. The container coupling mechanism 126 may be any now known or hereafter developed mechanism for coupling the cap 120 to the non-sterile container 20. For example, the container coupling mechanism 126 may be in the form of a threaded cap, a rubber stopper, a snap cap over a regular cap, a press-fit cap, or any other engagement arrangement that couples the cap 120 to the non-sterile container 20. In one example embodiment, as illustrated in FIGS. 2-5, the container coupling mechanism 126 may be in the form of a snap-fit coupling.

In some embodiments, the enclosure 140 may be sized to accommodate non-sterile containers of a variety of different sizes. That is, the enclosure 140 may be long enough (measured from the first end 142 to the second end 144) to accept non-sterile containers 20 of different sizes (i.e., lengths). The disclosed sealing mechanism 150 enables the enclosure 140 to be folded back upon itself (once the non-sterile container 20 has been disposed inside) and sealed at any position along the length of the enclosure, thus accommodating non-sterile containers of different lengths/sizes. It is also envisioned that a plurality of differently sized cap and drape systems 100 may be manufactured and/or provided. For example, it is envisioned that the cap and drape systems 100 may be provided with a number of different sized caps 120 for coupling to a variety of containers having different sized neck portions. Alternatively, it is envisioned that the cap 120 may include different features such as a threaded cap, a rubber stopper, a press-fit cap, or the like for accepting, and coupling to, a plurality of different non-sterile containers having different neck sizes.

Figure 3:
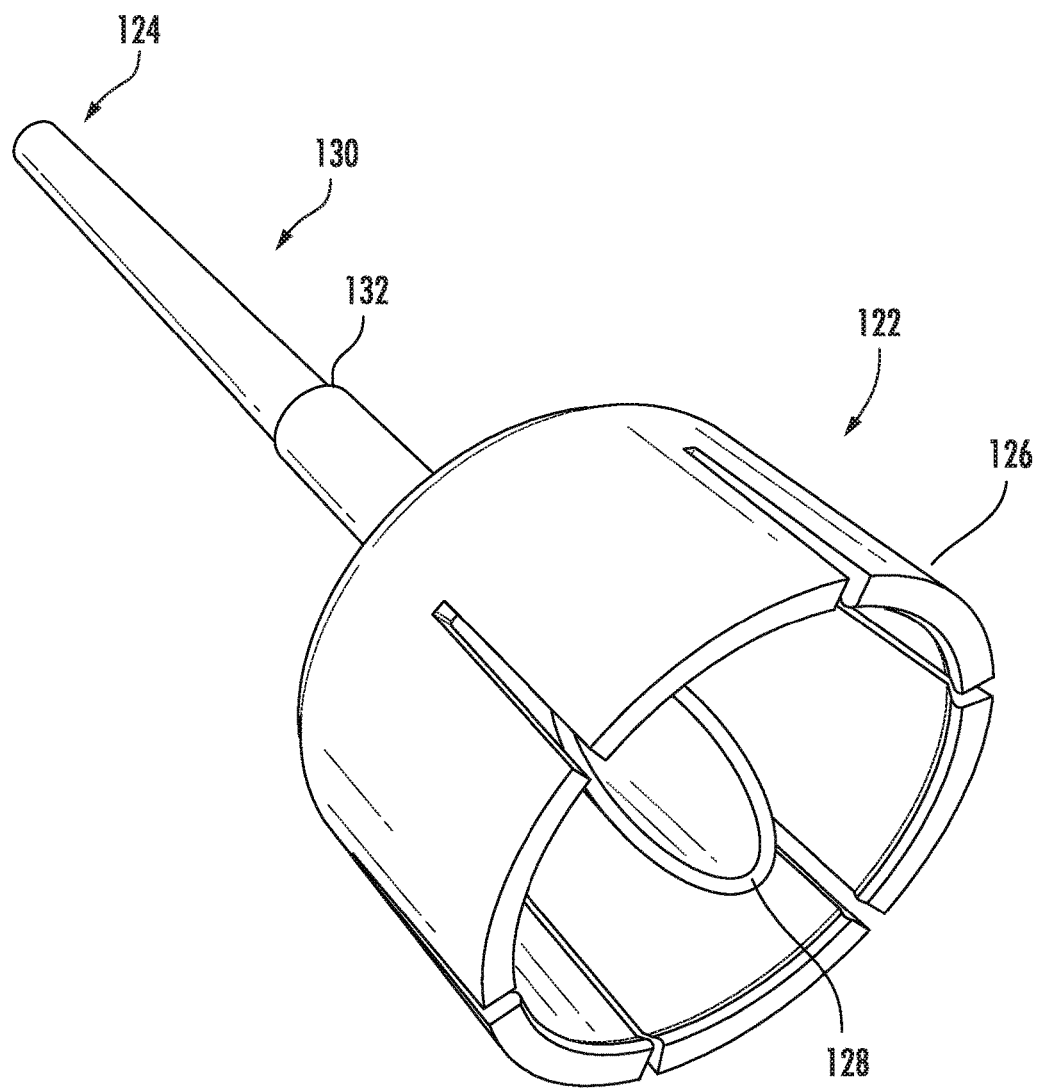
FIG. 3 illustrates a perspective view of an example embodiment of a cap used in connection with the cap and drape system shown in FIG. 2.
Figure 4:
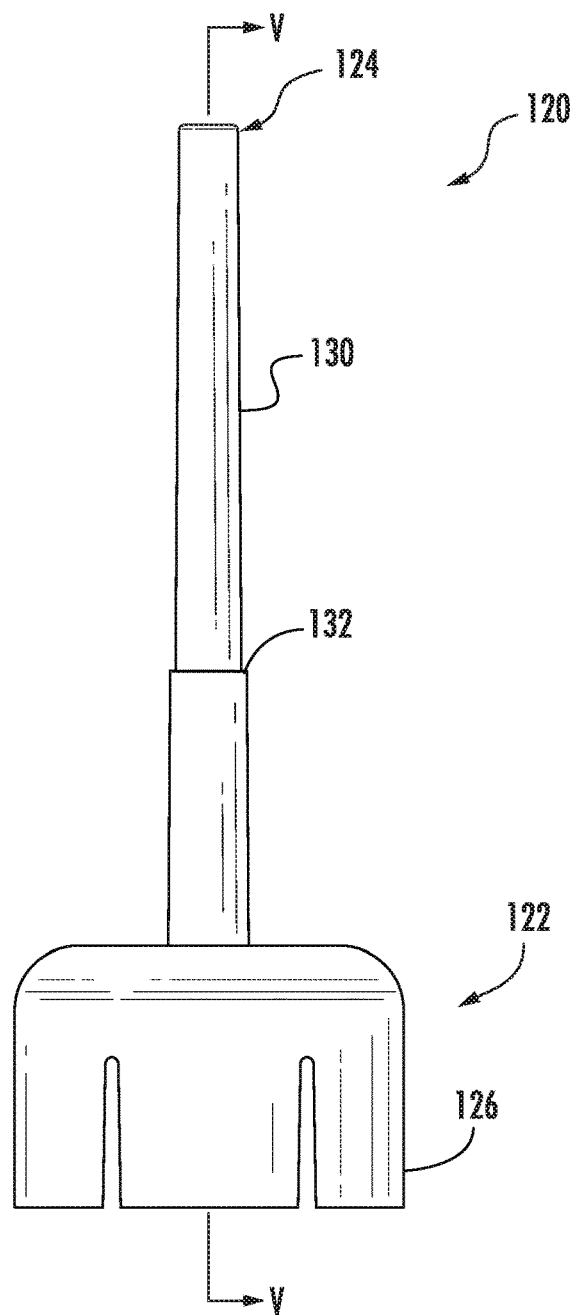
FIG. 4 illustrates a side view of the cap shown in FIG. 3.
Figure 5:
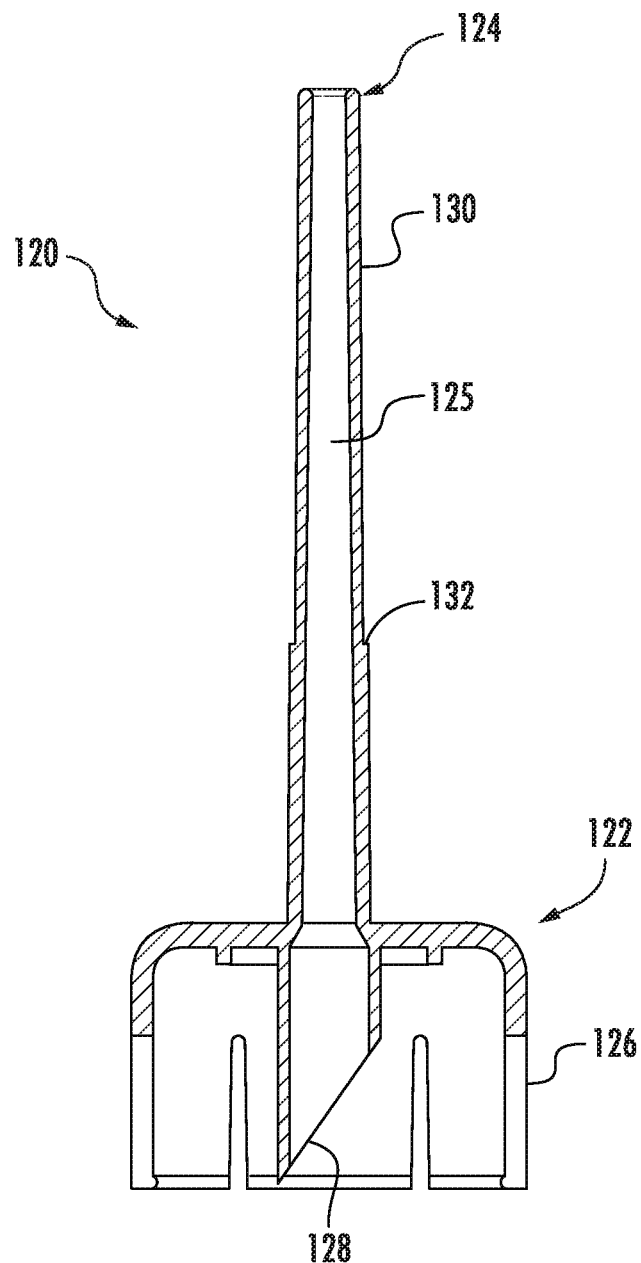
FIG. 5 illustrates a cross-sectional view of the cap shown in FIG. 3, the cross-sectional view taken along line V-V in FIG. 4.

In one exemplary non-limiting embodiment, illustrated in FIGS. 3-5, the first end 122 of the cap 120 may include a seal piercing mechanism 128 which, in use, can pierce a seal of the non-sterile container as the cap 120 is coupled to the container, thus placing the cap in fluid communication with the liquid product located within the container 20. The seal piercing mechanism 128 may, in some embodiments, be in the form of a spiked tip (e.g., similar to an IV spike), to facilitate piercing of the seal, although other seal piercing mechanisms are also envisioned. Further, although the illustrated embodiment includes a seal piercing mechanism 128, such a feature is not critical, and the cap and drape system 100 can be employed with a cap 120 that does not includes such a piercing mechanism. In such applications, the seal of the non-sterile container may simply be removed via a separate step.

Referring again to FIGS. 1, 2 and 4, the cap and drape system 100 may also include a splash guard 175, which may be selectively disposable about the nozzle 130 of the cap 120. The splash guard 175 may be manufactured from any suitable material, including, for example, a plastic material.

As illustrated, the splash guard 175 may include an opening 177 for receiving the nozzle 130 of the cap 120 so that the splash guard is mounted on the cap. In some embodiments, the nozzle 130 may be tapered such that it is of greater diameter near the first end 122 of the cap, and of smaller relative diameter near the second end 124 of the cap. The nozzle 130 may include a ridge 132 disposed intermediate the first and second ends 122, 124. In the illustrated embodiment the ridge may be formed by a step-change increase in the diameter of the nozzle. In use, the nozzle 130 of the cap 120 may be inserted into the opening 177 in the splash guard 175. During packaging (i.e., when the cap and drape system 100 is placed in the sterile pouch for storage and delivery), the splash guard 175 may be provisionally engaged with the nozzle 130 so that the splash guard can lie flat with the rest of the cap and drape system 100). For use, when the cap and drape system 100 is removed from the pouch in the sterile environment, the splash guard 175 may be press-fit to the nozzle 130 until, for example, the splash guard 175 engages the ridge 132 formed on the nozzle 130. As such, in this "use" position, the splash guard 175 may be perpendicularly positioned and locked in place. As will be appreciated, the splash guard 175 may protect the user from spray or reflection of the liquid product during use, thus providing an added safety feature for the user. The nozzle 130 may be manufactured from any suitable material such as, for example, a plastic, a metal, etc.

Figure 6:
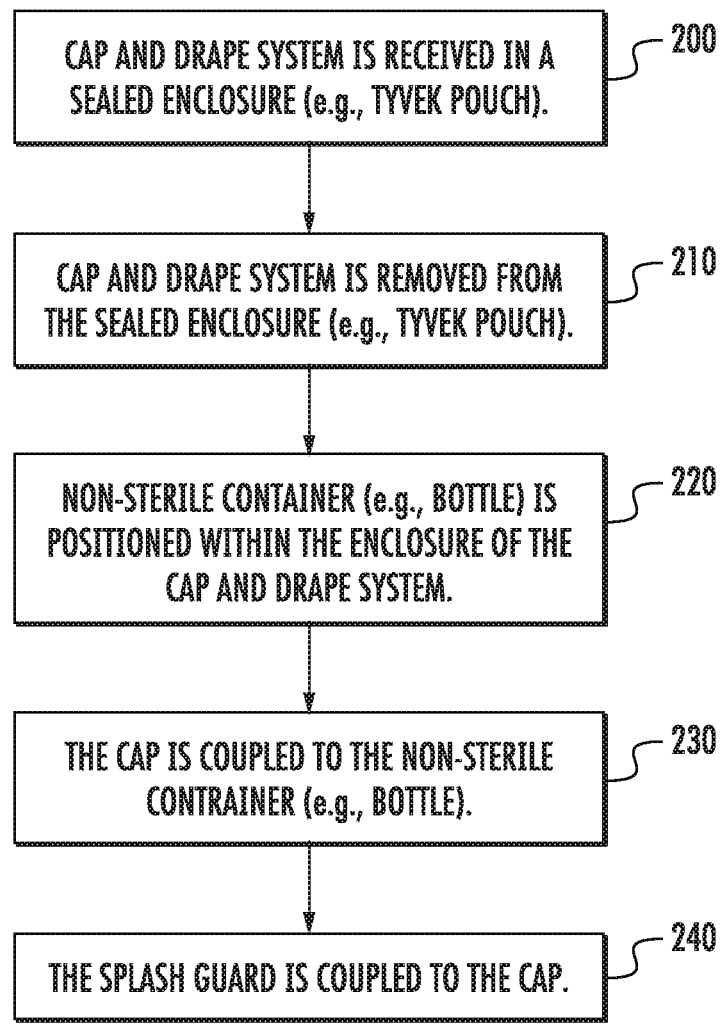
FIG. 6 illustrates a flowchart of an example embodiment of a method of use according to the disclosure.

Referring to FIG. 6, an example embodiment of a method of using the disclosed cap and drape system 100 will be described. In one example embodiment, at 200, the cap and drape system 100 may be pre-sterilized and delivered to the sterile environment. Alternatively, the cap and drape system 100 may be delivered to a user and then sterilized prior to entering the sterile environment. In one example embodiment, the cap and drape system 100 may be delivered in a sterile sealed envelope or pouch, such as, for example, a Tyvek pouch, although other mechanisms for delivering the cap and drape system 100 in a sterilized form are envisioned.

At 210, the user, for example, medical personnel, may remove the sterilized cap and drape system 100 from the sealed envelope. At 220, the first end 142 of the enclosure 140 can be opened and the non-sterile container 20 (e.g., a non-sterile glass bottle) can be introduced into the interior cavity 146 of the enclosure 140. The enclosure 140 may be coupled to the non-sterile container 20 by exposing a sealing mechanism 153 on an inner surface of the enclosure and pressing the sealing mechanism against the enclosure. The enclosure 140 may then be sealed around the non-sterile container 20 by folding over a portion of the first end 142 of the enclosure. In one example embodiment, a tape strip 154 may be removed from an adhesive strip disposed on the flap portion 152 of the enclosure 140, and the first end 142 of the enclosure may be folded over to engage the adhesive strip with an outer surface of the enclosure at a desired location. At 230, the medical personnel can couple the cap 120 attached to the enclosure 140 to the container 20, for example, by pressing the cap 120 into engagement with the neck portion 22 of the container 20, thus placing the liquid product within the container 20 into fluid communication with the cap 120. At 240, the medical personnel may couple the splash guard 175 to the cap 120 by pressing the splash guard 175 into engagement with the ridge 132 of the nozzle 130.

Using the disclosed system and method, a non-sterile container or bottle 20 can be completely sealed within a sterile volume so that the non-sterile container 20 can be introduced and/or used with a sterile environment.

While certain example embodiments of the disclosure have been described herein, it is not intended that the disclosure be limited to the specific embodiments described herein. For example, while certain example embodiments have been described as containing certain features, circuitry, and/or functionality, one of ordinary skill in the art will appreciate that features, circuitry, and/or functionality can be interchangeable amongst the various disclosed embodiments. Therefore, the above description should not be construed as limiting, but merely as exemplifications of particular embodiments. Those skilled in the art will envision additional modifications, features, and advantages within the scope and spirit of the claims appended hereto.

What is claimed is:

1. A device for enclosing a non-sterile container to enable introduction of the container into a sterile environment, the device comprising:
    a drape having an interior cavity for receiving a non-sterile container therein creating a sterile barrier; and
    a cap coupled to the drape, the cap having a first end configured to couple to the non-sterile container and a second end with a nozzle extending through the drape and across the sterile barrier, such that a liquid within the non-sterile container can be expelled through the nozzle of the cap.

2. The device of claim 1, wherein the drape includes a first end and a second end, the interior cavity extending from the first end to the second end.

3. The device of claim 2, wherein the first end of the drape includes an opening for receiving the non-sterile container.

4. The device of claim 3, wherein the first end of the drape further comprises a sealing mechanism for sealing the opening when the non-sterile container is positioned within the interior cavity.

5. The device of claim 4, wherein the sealing mechanism comprises an adhesive strip.

6. The device of claim 2, wherein the nozzle has a first end, a second end, and a thru-bore extending from the first end to the second end.

7. The device of claim 6, wherein the second end of the drape is sealed to the cap so that the first end of the cap is positioned within the interior cavity of the drape and the nozzle extends through an opening in the drape so that the second end of the cap is positioned outside of the drape.

8. The device of claim 7, wherein the first end of the cap includes a container coupling mechanism for engaging the non-sterile container positioned within the interior cavity of the drape.

9. The device of claim 8, wherein the container coupling mechanism is in the form of a threaded cap, a rubber stopper, or a press-fit cap.

10. The device of claim 8, wherein the first end of the cap includes a seal piercing mechanism so that, in use, coupling the cap to the non-sterile container causes the seal piercing mechanism to pierce a seal located on the non-sterile container to place the cap in fluid communication with the liquid located within the non-sterile container.

11. The device of claim 6, further comprising a splash guard for coupling to the cap.

12. The device of claim 11, wherein the splash guard includes an opening for receiving the nozzle of the cap.

13. The device of claim 12, wherein the nozzle includes a ridge, the splash guard engageable with the ridge when the splash guard is pressed toward the first end of the cap.

14. A method for introducing a non-sterile container containing a sterile liquid into a sterile environment, the method comprising:
    inserting a non-sterile container into an interior cavity of a sterile cap and drape device;
    sealing the cap and drape device about the non-sterile container to seal the non-sterile container within the interior cavity of the cap and drape device creating a sterile barrier;
    coupling a cap to the non-sterile container the cap having a first end configured to couple to the non-sterile container and a second end with a nozzle extending through the drape and across the sterile barrier; and
    via the cap, dispensing the sterile liquid through the nozzle of the cap within the sterile environment.

15. The method of claim 14, further comprising coupling a splash guard to the cap by pressing the splash guard into engagement with a nozzle of the cap, the splash guard having an opening for receiving the nozzle therethrough, the nozzle having a ridge for seating the splash guard thereon.

16. The method of claim 14, wherein coupling the cap to the non-sterile container comprises coupling a container coupling mechanism formed on a first end of the cap to the non-sterile container.

17. The method of claim 16, further comprising adhering an inner surface of the cap and drape device to an outer surface of the non-sterile container.

18. The method of claim 14, further comprising adhering an inner surface of the cap and drape device to the non-sterile container.

19. The method of claim 14, wherein sealing the cap and drape device about the non-sterile container comprises adhering a portion of the cap and drape device to itself.

20. The method of claim 19, wherein adhering a portion of the cap and drape device to itself comprises removing a tape strip adhesive strip disposed on a flap portion of a first end of the drape, and pressing the adhesive strip and flap portion against an outer surface of the cap and drape device.

* * * * *